United States Patent [19]
von Bredow et al.

[11] 4,066,437
[45] Jan. 3, 1978

[54] TRIAZOLIDINE COMPOUNDS USEFUL AS HERBICIDES

[75] Inventors: Brigitta von Bredow, Binningen, Switzerland; Georg Pissiotas, Lorrach, Germany

[73] Assignee: Ciba-Geigy Corporation, Ardsley, N.Y.

[21] Appl. No.: 715,354

[22] Filed: Aug. 18, 1976

[30] Foreign Application Priority Data

Aug. 29, 1975 Switzerland .................. 11247/75

[51] Int. Cl.² .................. A01N 9/22; C07D 513/04
[52] U.S. Cl. .................. 71/91; 260/308 C; 424/272
[58] Field of Search .................. 260/308 C; 71/91

[56] References Cited
PUBLICATIONS

Zinner — C.A. 65, 719a, (1966), Abstract of Arch. Pharm. 299(4), pp. 312–314, (1966).

Primary Examiner—Raymond V. Rush
Attorney, Agent, or Firm—Harry Falber

[57] ABSTRACT

The present invention relates to 1,2,4-triazolidine compounds, to a process for producing them, to their use for controlling vegetable and animal pests in agriculture, and to compositions, which contain these 1,2,4-triazolidine compounds as active substance.

The 1,2,4-triazolidine compounds correspond to formula

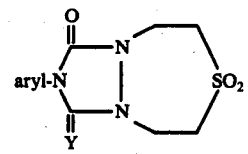

wherein
aryl is an aryl group other than benzene, and
Y is an oxygen or sulphur atom.

10 Claims, No Drawings

TRIAZOLIDINE COMPOUNDS USEFUL AS HERBICIDES

The present invention relates to novel 1,2,4-triazolidine compounds, to a process for producing them, to their use as active substances for combatting pests, also to compositions for combatting vegetable and animal pests in agriculture, which compositions contain these novel 1,2,4-triazolidine compounds.

The novel 1,2,4-triazolidine compounds correspond to formula I

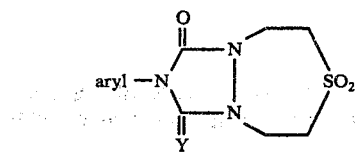

wherein
aryl is an aryl group other than benzene, and
Y is an oxygen or sulphur atom.

By aryl group in this formula is meant a substituted phenyl ring or a substituted or unsubstituted naphthyl ring.

These rings can be mono- or polysubstituted by a halogen atom, a lower alkyl, lower alkoxy, lower alkylthio, lower alkenyloxy or lower alkynyloxy group, an aryloxy or aralkoxy group, the trifluoromethyl group, a di-lower-alkyl-sulphamoyl group, the sulphamoyl group, the nitro, amino, cyano or thiocyano group, a mono- or di-lower-alkylamino group, a di-lower-alkylcarbamoyl group or a lower-alkylsulphonyl group.

The term "lower" before alkyl, alkenyl or alkynyl groups serves to indicate that these groups in general contain up to 4 carbon atoms. The aryloxy group can contain both a phenyl group and an aryl group, according to the definition given hereinbefore. By an araloxy group is meant preferably a benzyl or phenylethyl group, which can be unsubstituted or substituted as defined.

The compounds of formula I are produced by processes known per se; for example by condensing a 1,2,4-triazolidine-3,5-dione or 1,2,4-triazolidine-3-thia-5-one of formula II $$\text{aryl} - N \underset{Y}{\overset{O}{\diagdown}} \begin{array}{c} NH \\ | \\ NH \end{array} \quad (II),$$

wherein aryl and Y have the aforesaid meanings, with divinylsulphone $(CH_2=CH)_2SO_2$.

This condensation or addition is best performed in a polar aprotic organic solvent, in the presence of an amount of base as catalyst; see in this respect G. Zinner Arch. Pharm. 299 (1966), pp. 312 – 314, wherein there is described, e.g., the production of 9-phenyl-8,10-dioxo-4,1,7,9-thiadiabicyclo [5.3. 0]decane-4,4-dioxide.

Polar aprotic organic solvents which are suitable for this condensation reaction are, e.g., formamides, aralkylsulphoxides, cyclic ketones, lower alkanols or nitriles.

This condensation or addition reaction is catalysed by the addition of an amount of base, such as alkanolic KOH or NaOH. The temperature can vary in the process between 0° C and 150° C.

The starting materials of formula II are in some cases known but for the main part are novel. The production of 1,2,4-phenyl-1,2,4-triazolidine-3,5-dione, also known as 4-phenylurazole or N-phenylimide of azodicarboxylic acid, has already been described by J. Thiele et al., Ann. 283 (1894), p.1. Further references in this connection are J. Stolle Ber. 45 (1912) p. 273; G. Zinner et al., Arch. Pharm. 294 (1961), pp. 370–372; as well as R. C. Cockson et al., Tetrahedron Letters 14 (1962), pp. 615-618. For example, 1-ethoxycarbonyl-4-phenyl-semicarbazide, $C_2H_5-O-CO-NH-NH-CO-NH-C_6H_5$, is cyclised in a hot alkaline medium, and 4-phenyl-1,2,4-triazolidine-3,5-dione is then isolated from an acid medium, from which it has precipitated in crystalline form.

1-Ethoxycarbonyl-4-phenyl-semicarbazide, or similar semicarbazides or thiosemicarbazides of formula III alkyl—O—CO—NH—NH—CY—NH-aryl          (III)

wherein alkyl is a lower alkyl group and aryl is an aryl group as defined hereinbefore, which are required for the production of 1,2,4-triazole-3-oxo-5-one or 1,2,4-triazole-3-thia-5-one of formula II, can be obtained by reaction of hydrazine hydrate with the equimolar amount of diethyl carbonate or of another dialkyl carbonate; and reaction of the resulting alkyl carbazate with the equimolar amount of an arylisocyanate or arylisothiocyanate, wherein aryl has the meaning defined hereinbefore.

The compounds of formula I can be produced by the following sequence of reactions:

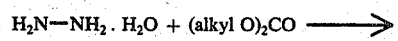

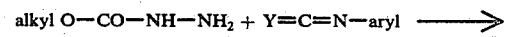

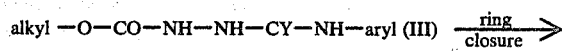

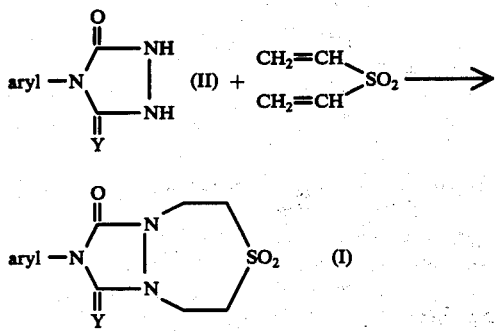

The compounds of formula I are suitable for combatting various animal and vegetable pests: they can be used, for example, for combatting insects and spiders.

Some of these compounds also have a bactericidal action, or are effective against phytopathogenic fungi; and are suitable for the treatment of seed, fruits, tubers, etc., for protection against infestations.

The compounds of formula I also have an effect on abscission, and can be used to facilitate the harvesting of fruit, citrus fruits, berries, olives, nuts, etc.

Principally, however, the compounds of formula I have a herbicidal action, and are suitable for the control of weeds, particularly dicotyledenous weeds. It has been shown in this respect that the otherwise very resistant problematic weeds of the Galium family: galium plants such as Galium verum (yellow galium), Galium aparine (goose grass), Galium mollugo (common bedstraw), etc., against which the known herbicides are often inadequately effective, can be destroyed with the compounds of formula I. This applies particularly when they are applied before emergence of the plants.

A great advantage is that the novel compounds of formula I behave selectively with respect to many cultivated plants, such as cereals, maize or rice and also rape-seed; and can be used for combatting weeds in such crops.

The applied amounts of active substance are usually 1 to 6 kg per hectare of cultivated area; however, quite satisfactory results are obtained with application per hectare of only 1 to 2 kg in the form of a wettable-powder dispersion.

1,2,4-Triazolidine compounds of formula I which have proved particularly effective are those wherein aryl is a phenyl group substituted in the para position by halogen, $(C_1-C_4)$alkyl, $(C_1-C_4)$alkoxy, $(C_1-C_4)$alkylthio, $(C_2-C_4)$ alkenyloxy, $(C_2-C_4)$alkynyloxy, phenoxy, benzyloxy, trifluoromethyl, sulphamoyl, di$(C_1-C_4)$alkylsulphamoyl, nitro, cyano, thiocyanato, amino, mono- or di$(C_1-C_4)$alkylamino, carbamoyl, di$(C_1-C_4)$alkylcarbamoyl or $(C_1-C_4)$alkylsulphonyl.

These compounds of formula I are advantageously used not on their own but together with other herbicidally active substances which likewise do not unfavourably affect cultivated plants. The herbicidal activity can in that way be extended, with a relatively small applied amount of active substance, to control a wider range of weeds and to attain synergistic effects. The herbicides from the class comprising substituted ureas or substituted triazines, as well as various other herbicides, have proved particularly suitable when applied in combination with the compounds of formula I.

The following compounds are especially suitable as constituents of a mixture with the compounds of formula I.

SUBSTITUTED UREAS

N-(3,4-dichlorophenyl)-N',N'-dimethylurea,
N-(4-chlorophenyl)-N'-methoxy-N'-methylurea,
N-(4-chlorophenyl)-N'-isobutynyl-N'-methylurea,
N-(3,4-dichlorophenyl)-N'-methoxy-N'-methylurea,
N-(4-bromophenyl)-N'-methoxy-N'-methylurea,
N-[4-(chlorophenoxy)-phenyl]-N',N'-dimethylurea,
N-benzothiazol-2-yl-N,N'-dimethylurea,
N-benzothiazol-2-yl-N'-methylurea,
N-(3-trifluoromethylphenyl)-N',N'-dimethylurea,
N-(3,4-dichlorophenyl)-N'-methyl-N'-butylurea,
N-(3-chloro-4-ethylphenyl)-N',N'-dimethylurea,
N-(3-chloro-4-methylphenyl)-N',N'-dimethylurea,
N-(3-chloro-4-ethoxyphenyl)-N'-methyl-N'-methyl-N'-methoxyurea,
N-(3-chloro-4-methoxyphenyl)-N',N'-dimethylurea,
N-(hexahydro-4,7-methanoidan-5-yl)-N',N'-dimethylurea,
N-(3,4-dichlorophenyl)-N'-n-propylurea,
N-(3-chloro-4-trifluoromethyl-phenyl)-N'-methyl-N'-methoxyurea,
N-(3-chloro-4-isopropylphenyl)-N'-methyl-N-methoxyurea,
N-4-fluorophenyl-N'-carboxymethoxy-N'-methylurea,

SUBSTITUTED TRIAZINES 2-chloro-4,6-bis(ethylamino)-s-triazine,
2-chloro-4-ethylamino-6-isopropylamino-s-triazine,
2-methylmercapto-4,6-bis(isopropylamino)-s-triazine,
2-methylmercapto-4,6-bis(ethylamino)-s-triazine,
2-methylmercapto-4-ethylamino-6-tert.butylamino-triazine,
2-methylmarcapto-4-ethylamino-6-isopropylamino-s-triazine,
2-methylmercapto-4-methylamino-6-isopropylamino-s-triazine,
2-chloro-4,6-bis(isopropylamino)-s-triazine,
2-azido-4-methylmercapto-6-isopropylamino-s-triazine,
2-chloro-4-isopropylamino-6-(γ-methoxypropylamino)-s-triazine,
2-chloro-4-isopropylamino-6-(γ-methoxypropylamino)-s-triazine,
2-(6-ethylamino-4-chloro-s-triazin-2-yl-amino)-2-methylpropionitrile,
2-methylmercapto-4-isopropylamino-6-(3'-methoxypropylamino)-s-triazine,
2-chloro-4-diethylamino-6-ethylamino-s-triazine,
2-chloro-4-ethylamino-6-sec.butylamino-s-triazine, 4-amino-6-tert.butyl-3-methylthio-1,2,4-triazin-5-(4H)-one,
2-methoxy-4-ethylamino-6-tert.butylamino-s-triazine,
2-ethylthio-4,6-bis-(isopropylamino)-s-triazine,
2-chloro-4-methylamino-6-tert.butylamino-s-triazine,
2-(6'-cyanopropylamino-4'-chloro-s-triazin-2'-yl-amino)-2-methylpropionitrile.

OTHER COMPOUNDS 2,6-dibromo-4-cyanophenol + esters,
2,4-dichlorophenoxyacetic acid + salts + esters,
2-(4'-chloro-2'-methylphenoxy)-propionic acid + salts + esters, trichloroacetic acid,
S-2,3-dichloroallyl-N,N-diisopropyl-thiolcarbamate,
S-2,3,3-trichloroallyl-N,N-diisopropyl-thiolcarbamate,
S-ethyl-N,N-diisobutyl-thiolcarbamate,
N,N-diethyl-S-(4-chlorobenzyl)-thiolcarbamate,
S-ethyl-N-cyclopropylmethyl-N-propyl-thiolcarbamate,
N-propylthiolcarbonyl-decahydroquinaldine
2-chloro-N-(2', 6'-diethylphenyl)-N-methoxymethyl-acetamide,
2-chloro-N-(2', 6'-dimethylphenyl)-N-methoxyethyl-acetamide,
2-chloro-N-(2',6'-dimethylphenyl)-N-(1''-methyl-2''-methoxyethyl)-acetamide,
2-chloro-N-(2'-methyl-6'-ethylphenyl)-N-(1'''-methyl-2''-methoxyethyl)-acetamide,
N,N-di-n-propyl-2,6-dinitro-4-trifluoromethyl-aniline,
N-cyclopropylmethyl-N-n-propyl-2,6-dinitro-4-trifluoromethyl-aniline.

The following Example serves to further illustrate the production of the novel 1,3,4-triazolidine compounds. The temperatures are given in degrees Centigrade.

EXAMPLE 1

9-p-Chlorophenyl-8,10-dioxo-4,1,7,9-thiatriazabicyclo[5.3.0]decane-4,4-dioxide 20 drops of 6N KOH and 118 g (0.1 mole) of divinylsulphone are added to a mixture, heated to 50°, of 21 g (0.1 mole) of 4-(p-chlorophenyl)urazole and 500 ml of ethanol. Stirring is maintained until the whole is in solution, and the solution is then refluxed for 8 hours. After cooling, the precipitated substance is filtered off with suction from the reaction solution and dried under vacuum to thus obtain 32 g (97% of theory) of 9-p-chlorophenyl-8,10-dioxo-4,1,7,9-thiatriazabicyclo[5.3.0]decane-4,4-dioxide, which has a melting point of above 240°.

Also the compounds contained in the following Table I are produced by this method:

Table I aryl—N$^9$ (ring structure with N$_7$, N$_1$, SO$_2$ at position 4, Y at position 10)

| No. | Y | Aryl | Physical constants |
|---|---|---|---|
| 1 | O | —C$_6$H$_4$—Cl | m.p. 240° (Example 1) |
| 2 | O | —C$_6$H$_3$(Cl)-Cl | m.p. 223° |
| 3 | O | —C$_6$H$_3$(Cl)-CF$_3$ | m.p. 187° |
| 4 | O | —C$_6$H$_3$(Cl)-Cl | m.p. 245° |
| 5 | O | —C$_6$H$_4$—CF$_3$ | m.p. 221° |
| 6 | O | —C$_6$H$_3$(F)-CF$_3$ | m.p. 178° |
| 7 | O | —C$_6$H$_4$—OC$_4$H$_9$ | m.p. 196–197° |
| 8 | O | —C$_6$H$_3$(Cl)-CH$_3$ | m.p. 211° |
| 9 | O | —C$_6$H$_4$—CH$_3$ | m.p. 287° |
| 10 | O | —C$_6$H$_3$(Cl)-CF$_3$ | m.p. 187° |
| 11 | O | —C$_6$H$_3$(Cl)-CH(CH$_3$)$_2$ | m.p. 186° |
| 12 | O | —C$_6$H$_3$(Cl)-Cl | |
| 13 | O | —C$_6$H$_3$(Cl)-CF$_3$ | |
| 14 | O | —C$_6$H$_4$—Br | m.p. 290° |
| 15 | O | —C$_6$H$_3$(CH$_3$)-CH$_3$ | |
| 16 | O | —C$_6$H$_4$—OCH$_3$ | m.p. 265° |
| 17 | O | —C$_6$H$_4$—SCH$_3$ | |
| 18 | O | —C$_6$H$_3$(CH$_3$)-NO$_2$ | m.p. 295–296° |
| 19 | O | —C$_6$H$_4$—CN | |
| 20 | O | —C$_6$H$_4$—N(CH$_3$)$_2$ | |
| 21 | O | —C$_6$H$_4$—CH(CH$_3$)$_2$ | |
| 22 | O | naphthyl | m.p. 236–237° |

Table I-continued aryl—N(9)... structure with N(7), N(6), N(5), SO₂(4), N(1,2,3), Y groups

| No. | Y | Aryl | Physical constants |
|-----|---|------|-------------------|
| 23 | S | ⟨C₆H₄⟩-Cl | |
| 24 | S | ⟨C₆H₃⟩(Cl)(Cl) | |
| 25 | S | ⟨C₆H₄⟩-CH₃ | |
| 26 | O | ⟨C₆H₃⟩(CF₃)(CF₃) | m.p. 135 – 136° |
| 27 | S | ⟨C₆H₄⟩-SCH₃ | |
| 28 | O | ⟨C₆H₄⟩-Br | m.p. 240° |
| 29 | O | ⟨C₆H₃⟩(F)(Cl) | m.p. 230° |
| 30 | O | ⟨C₆H₃⟩(CH₃)(Cl) | m.p. 243° |
| 31 | O | ⟨C₆H₃⟩(CH₃)(Cl) | m.p. 275° |
| 32 | O | ⟨C₆H₄⟩-O-⟨C₆H₄⟩-Cl | m.p. 214 – 215° |
| 33 | O | ⟨C₆H₄⟩-CF₃ | m.p. 265° |
| 34 | O | ⟨C₆H₃⟩(CF₃)(OC₂H₅) | m.p. 168 – 169° |
| 35 | O | ⟨C₆H₃⟩(OC₂H₅) | m.p. 104 – 105° |
| 36 | O | ⟨C₆H₃⟩(OC₂H₅)(CF₃) | m.p. 220 |

The following tests were carried out in order to verify the herbicidal action:

a. ACTION AGAINST WEEDS IN GENERAL

The following weeds were sown in pots in a greenhouse:

| | |
|---|---|
| Avena fatua | wild oat |
| Lolium perenne | perennial ryegrass |
| Alopecurus myos. | slender foxtail |
| Galium aparine | goose grass |
| Sinapis alba | white mustard |
| Chrysanthemum segetum | corn marigold |
| Stellana media | chickweed |

One day after sowing, the pots were treated with a spray liquor of compound No. 1 in such a manner that the amounts of active substance sprayed on were 4, 2 and 1 kg per hectare, respectively. The pots were then kept in a greenhouse at 20°-23° C, 50-70% relative humidity, with regular watering, in order to render optimum growth of the plants possible. The test was evaluated after 4 weeks and the condition of the plants was assessed according to the following ratings:

9: plant thrives normally in the same way as the control plant,
8–6: increasing degrees of slight reversible damage,
5: permanent damage,
4 – 2: increasing amount of stunting
1: plant dead.

| | Applied amount kg/h * | | |
|---|---|---|---|
| Plants | 4 | 2 | 1 |
| wheat | 4 | 5 | 6 |
| barley | 5 | 5 | 6 |
| Avena fatua | 3 | 3 | 5 |
| Lolium perenne | 4 | 4 | 5 |
| Alopecurus myos. | 3 | 3 | 5 |
| Galium aparine | 2 | 2 | 2 |
| Sinapis alba | 2 | 5 | 5 |
| Chrysanthemum segetum | 3 | 3 | 3 |
| Stellana media | 4 | 6 | 6 |

* = kg per hectare b. ACTION AGAINST GALIUM APARINE

Winter wheat of the "Probus" variety and the weed Galium aparine were sown in pots in a greenhouse. In the case of the Galium, different pots were used to give seed depths of 1, 3 and 5 cm, respectively. One day after sowing, the pots were treated with a spray liquor of the compound No. 1 in such a manner that the amounts of active substance applied were 4, 2, 1 and ½ kg per hectare, respectively. The pots were subsequently kept in the greenhouse under the aforementioned conditions, and the test was likewise evaluated after 4 weeks.

| | Applied amounts in kg/hectare | | | |
|---|---|---|---|---|
| Plants | 4 | 2 | 1 | ½ |
| wheat | 7 | 8 | 9 | 9 |
| Galium, seed depth 1 cm | 1 | 2 | 2 | 2 |
| Galium, seed depth 3 cm | 2 | 3 | 3 | 3 |
| Galium, seed depth 5 cm | 2 | 3 | 4 | 4 |

The compound No. 1 has an excellent action against Galium aparine, without at the same time damaging the wheat.

c. FIELD TEST IN WHEAT CROPS

A field divided into plots is sown in September with winter wheat of the "Zenith" variety. Between the plots are left strips on which the weeds can be observed. Shortly after sowing, but before germination of the wheat, the plots and the adjacent 'weed' strips are sprayed with emulsions of the active substances in such a way that the applied amounts are 4, 2, 1.5 and 1 kg of active substance per hectare, respectively. Certain plots remain untreated and serve as control plots. The plots are firstly evaluated in late autumn, when the plants are still small (4–6 leaves), and again in the late spring, at the time of maximum growth. The evaluation is carried out according to the following criteria: damage to the wheat; condition of the most important weeds; and percentage area overgrown with weeds. The condition of the plants is assessed on the basis of the following ERWC scale:

| Rating | Crop | Weed |
|---|---|---|
| 1 | thrives normally | destroyed |
| 2 – 4 | slight damage | severe damage |
| 5 | unsatisfactory | unsatisfactory |
| 6 – 8 | severe damage | slight damage |
| 9 | destroyed | thrives normally |

In this test, the compound No. 1 is tested on its own and together with the herbicides "Dicuran" (chlorotolurone=N-(3-chloro-4-methylphenyl)-N', N'-dimethylurea) and "Igran" (terbutryn=2-methyl-4-ethylamino-6-t.butylamino-s-triazine). The results are summarised in the following Tables. The given values are mean values obtained from several plots.

| Tested compound or mixture | Test at Satigny (Geneva) Switzerland | | | | | | | | | | | | | |
|---|---|---|---|---|---|---|---|---|---|---|---|---|---|---|
| | Compound No. 1 | | | | Dicuran | | Igran | | Mixture: Comp. No. 1 + Dicuran | | | Mixture: Comp. No. 1 + Ingran | | |
| applied amount in kg/hectare | 1 | 1.5 | 2 | 4 | 1.5 | 2 | 1.5 | 2 | 2+1.5 | 1.5+2 | 2+2 | 2+1.5 | 1.5+2 | 2+2 |
| evaluation after 33 days | | | | | | | | | | | | | | |
| weed strip % overgrown | 10 | 8.3 | 10 | 10 | 10 | 8.3 | 10 | 7 | 8.33 | 9.3 | 7 | 10 | 9.3 | 10 |
| winter wheat | 1 | 1 | 1 | 1 | 1 | 1 | 1 | 1 | 1 | 1 | 1 | 1 | 1 | 1 |
| Alopecurus myosuroides | 8 | 6 | 7 | 4 | 4 | 4 | 6 | 4 | 4 | 4 | 4 | 4 | 5 | 3 |
| Galium aparine | 7 | 3 | 3 | 2 | 9 | 9 | 9 | 9 | 4 | 3 | 2 | 3 | 5 | 4 |
| evaluation after 187 days | | | | | | | | | | | | | | |
| weed strip % overgrown | 100 | 88.3 | 95 | 86.7 | 93.3 | 90 | 95 | 8.33 | 85 | 96.7 | 83.3 | 100 | 90 | 80 |
| cereal plot % weeds | 93.3 | 73.3 | 76.7 | 50 | 66.7 | 53.3 | 70 | 50 | 21.7 | 11.7 | 7.3 | 41.7 | 30 | 35 |
| winter wheat | 1 | 1 | 1 | 1 | 2 | 4 | 1 | 1 | 2 | 4 | 4 | 1 | 3 | 1 |
| Alopecurus myosuroides | 9 | 9 | 9 | 8 | 7 | 4 | 8 | 7 | 6 | 4 | 3 | 8 | 6.5 | 7 |
| Galium aparine | 7 | 4 | 3 | 1 | 9 | 9 | 9 | 9 | 2 | 3 | 2 | 4 | 3 | 3 |
| Veronica persica | 3 | 1 | 1 | 1 | 9 | 9 | 8 | 9 | 1 | 1 | 1 | 1 | 1 | 1 |
| Veronica hederaefolia | 85.5 | 5 | 5 | 1 | 9 | 9 | 8 | 9 | 5 | 6 | 7 | 6 | 5.5 | 5 |

| Tested compound or mixture | Test at Montagny la Ville (FR) Switzerland | | | | | | | | | | |
|---|---|---|---|---|---|---|---|---|---|---|---|
| | Compound No. 1 | | | | Igran | | Compound No. 1 + Igran | | | | |
| applied amount in kg/hectare | 1 | 1.5 | 2 | 4 | 1 | 1.5 | 1+1.5 | 2+1 | 1.5+1 | 1.5+1.5 | 1.5+2 |
| evaluation after 42 days | | | | | | | | | | | |
| weed strip % overgrown | 5 | 5 | 5 | 5 | 5 | 5 | 5 | 5 | 5 | 5 | 5 |
| cereal plot % weeds | 1 | 3 | 1 | 1 | 2 | 2 | 1 | 1 | 1 | 1 | 1 |
| winter wheat | 1 | 1 | 1 | 4 | 1 | 1 | 1 | 1 | 1 | 1 | 1 |
| Galium aparine | 4 | 3 | 3 | 1 | 6 | 6 | 3 | 1 | 1 | 3 | 3 |
| Viola tricolor | 3 | 1 | 1 | 3 | 1 | 4 | 1 | 1 | 1 | 1 | 1 |
| evaluation after 210 days | | | | | | | | | | | |
| weed strip % overgrown | 20 | 20 | 20 | 20 | 20 | 20 | 20 | 20 | 20 | 20 | 20 |
| cereal plot % weeds | 1.3 | 1 | 2 | — | 8.3 | 4 | 1 | 1 | 1 | 1 | 1 |
| winter wheat | 1 | 1 | 1 | 3 | 1 | 1 | 1 | 1 | 1 | 1 | 1 |
| Galium aparine | 1 | 2 | 2 | 1 | 7 | 6 | 3 | 3 | 2 | 3 | 3 |
| Viola tricolor | 3 | 3 | 2 | 1 | 6 | 4 | 3 | 1 | 1 | 3 | 1 |
| Arabidopsis thaliana | 1 | 1 | 1 | 1 | 3 | 3 | 1 | 1 | 1 | 1 | 1 |
| Papaver rhoeas | 1 | 3 | 1 | 1 | 3 | 1 | 1 | 1 | 1 | 1 | 1 |

These tests show that Galium in wheat crops, which is combatted by the herbicides "Dicuran" and "Igran" either unsatisfactorily or not at all, can be brought well under control by the compound No. 1 or by admixtures thereof with "Dicuran" or "Igran".

The compositions according to the invention are produced in a manner known per se by the intimate mixing and/or grinding of the active substances with suitable carriers, optionally with the addition of dispersing agents or solvents which are inert to the active substances. The active substances can be obtained and used in the following forms:

solid preparations: dusts, scattering agents, granulates (coated granulates, impregnated granulates and homogeneous granulates);
water-dispersible concentrates of active substance: wettable powders pastes, emulsions and flowables;
liquid preparations: solutions.

The solid preparations (dusts, scattering agents and granules) are produced by mixing the active substances with solid carriers. Suitable carriers are, e.g.: kaolin, talcum, bole, loess, chalk, limestone, ground limestone, attapulgite, dolomite, diatomaceous earth, precipitated silicic acid, alkaline-earth silicates, sodium and potassium aluminum silicates (feldspar and mica), calcium and magnesium sulphates, magnesium, oxide, ground synthetic materials, fertilisers such as ammonium sulphate, ammonium phosphate, ammonium nitrate, urea, ground vegetable products such as bran, bark dust, sawdust, ground nutshells, cellulose powder, residues of plant extractions, active charcoal, etc., singly or in admixture with one another.

The particle size of the carriers is for dusts advantageously up to about 0.1 mm and for granulates 0.2 mm or coarser.

The concentration of active substance in the solid preparations is 0.5 to 80%.

It is possible to add to these mixtures also additives stabilising the active substance, and/or nonionic, anionactive and cation-active substances which improve, e.g., the adhesiveness of the active substances on plants and on parts of plants (adhesives and agglutinants), and/or ensure better wettability (wetting agents) as well as dispersibility (dispersing agents). Suitable adhesives are, for example, olein/lime mixture, cellulose derivatives (methylcellulose, carboxymethyl cellulose), hydroxyethylene glycol ethers of monoalkyl and dialkyl phenols having 5 to 15 ethylene oxide radicals per molecule and 8 to 9 carbon atoms in the alkyl radical, ligninsulphonic acid, the alkali metal salts and alkaline-earth metal salts thereof, polyethylene glycol ethers (carbowaxes), fatty alcohol polyglycol ethers having 5 to 20 ethylene oxide radicals per molecule and 8 to 18 carbon atoms in the fatty alcohol moiety, condensation products of ethylene oxide, propylene oxide, polyvinylpyrrolidones, polyvinyl alcohols, condensation products of urea and formaldehyde, as well as latex products.

Water-dispersible concentrates of active substances, i.e. wettable powders, pastes and emulsion concentrates (flowables), are agents which can be diluted with water to obtain the desired concentration. They consist of active substances, carrier, optionally additives stabilising the active substance, surface-active substances, and anti-foaming agents and, optionally, solvents, thickening agents, antifreezing agents and preservatives. The concentration of active substance in these preparations is 5 – 80%.

The wettable powders and pastes are obtained by mixing and grinding the active substances with dispersing agents and pulverulent carriers, in suitable devices, until homogeneity is obtained. Suitable carriers are, e.g., those previously mentioned in the case of solid preparations. It is advantageous in some cases to use mixtures of different carriers. As dispersing agents it is possible to use, e.g.: condensation products of sulphonated naphthalene and sulphonated naphthalene derivatives with formadehyde, condensation products of naphthalene or of naphthalenesulphonic acids with phenol and formaldehyde, as well as alkali metal salts, ammonium salts and alkaline-earth metal salts of ligninsulphonic acid, also alkylarylsulphonates, alkali metal salts and alkaline-earth metal salts of dibutylnaphthalenesulphonic acid, fatty alcohol sulphates such as salts of sulphated hexadecanols, heptadecanols, and salts of sulphated fatty alcohol glycol ethers, the sodium salt of oleyl methyl tauride, ditertiary acetylene glycols, dialkyl dilauryl ammonium chloride, and fatty acid alkali-metal and alkaline-earth metal salts.

Suitable anti-foaming agents are, e.g., silicones.

The active substances are so mixed, ground, sieved and strained with the above mentioned additives that the solid constituent in the case of wettable powders has a particle size not exceeding 0.02 to 0.04 mm, and in the case of pastes not exceeding 0.03 mm. For the preparation of emulsion concentrates and pastes, dispersing agents are used such as those mentioned in the preceding paragraphs, organic solvents and water. Suitable solvents are, e.g., alcohols, benzene, xylenes, toluene, dimethylsulphoxide, N,N-dialkylated amides, N-oxides of amines, especially trialkylamines, and mineral oil fractions boiling in the range of 120° to 350° C. The solvents must be practically odourless, nonphytotoxic, inert to the active substances and not readily combustible.

Furthermore, the compositions according to the invention can be used in the form of solutions. For this purpose, the active substances are dissolved in suitable organic solvents, solvent mixtures, water, or mixtures of organic solvents with water. As organic solvents, it is possible to use aliphatic and aromatic hydrocarbons, their chlorinated derivatives, alkylnaphthalenes, mineral oils on their own or in admixture with one another. The solutions should contain the active substances in a concentration of 1 to 20%.

These solutions can be applied either by means of a propellent gas (as spray), or by means of special sprayers (as aerosol).

Preparations of the new active substance are described in the following. Parts are given as parts by weight.

GRANULATE

The following substances are used to produce a 6% granulate;

6 parts of 9-p-chlorophenyl-8,10-dioxo-4,1,7,9-thiatriazolebicyclo[5.3.0]decane-4,4-dioxide,
0.25 part of epichlorohydrin,
0.25 part of cetyl polyglycol ether,
3.5 parts of polyethylene glycol,
90 parts of kaolin (particle size 0.3 to 0.8 mm).

The active substance is mixed with epichlorohydrin and the mixture is dissolved in 6 parts of acetone; the polyethylene glycol and cetyl polyglycol ether are then added. The solution obtained in this way is sprayed onto kaolin, and the acetone is subsequently evaporated off in vacuo.

WETTABLE POWDER

The following constituents are used to produce (a) a 80% and (b) a 50% wettable powder:

(a)

80 parts of 9-p-chlorophenyl-8,10-dioxo-4,1,7,9-thiatriazolebicyclo[5.3.0[decane-4,4-dioxide,
5.0 parts of sodium lauryl sulphate ("Tensopol"),
4.5 parts of naphthalenesulphonic acid/phenolsulphonic acid/formaldehyde condensate 3:2:1,
10.5 parts of precipitated colloidal silicic acid;

(b)

50 parts of the above active substance,
5 parts of sodium dibutylnaphthylsulphonate, or sodium lignin sulphonate,
3 parts of naphthalenesulphonic acid/formaldehyde condensate,
20 parts of kaolin,
22 parts of Champagne chalk.

The active substance is absorbed onto the appropriate carriers, and the resulting material is then mixed and finely ground with the other constituents. Wettable powders having excellent wetting and suspension properties are obtained. It is possible to obtain from such wettable powders, by dilution with water, suspensions of the desired concentration of active substance.

Flowable

The following substances are used to produce a 50% flowable:

50 parts of (3,4-dichlorophenyl)-8,10-dioxo-4,1,7,9-

-continued

| | thiatriazolebicyclo[5.3.0]decane-4,4-dioxide, | |
|---|---|---|
| 5 | parts of ethylene glycol, | anti-freezing agent |
| 4 | parts of glycerin, | |
| 3.5 | parts of nonylphenoxy(poly(ethyleneoxy)-ethanol, | |
| 2 | parts of octylphenylpolyglycol ether, | |
| 0.5 | part of silicone oil (antifoaming agent), | |
| 0.1 | part of polysaccharide (thickening agent), | |
| 0.1 | part of pentachlorophenol-Na-salt (preservative), | |
| 34.8 | parts of tap water. | |

We claim:
1. A 1,2,4-triazolidine compound of formula I

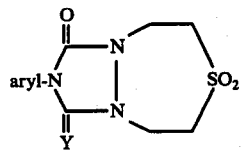

wherein
aryl is unsubstituted naphthyl, or naphthyl or phenyl mono- or di-substituted by halogen, ($C_1$–$C_4$) alkyl, ($C_1$–$C_4$)alkoxy, ($C_1$–$C_4$) alkylthio, ($C_2$–$C_4$) alkenyloxy, ($C_2$–$C_4$) alkynyloxy, phenoxy, benzyloxy, trifluoromethyl, sulphamoyl, di($C_1$–$C_4$)alkylsulphamoyl, nitro, cyano, thiocyanato, amino, mono- or di($C_1$–$C_4$)alkylamino, di($C_1$–$C_4$)alkylcarbamoyl or ($C_1$–$C_4$)alkylsulphonyl, and
Y is oxygen or sulfur.

2. The compound of claim 1, wherein one of said substituents on the mono- or di-substituted phenyl is present in the para-position.
3. The compound according to claim 1, 9-p-chlorophenyl-8,10-dioxo-4,1,7,9-thiatriazabicyclo-[5.3.0]-decane-4,4-dioxide.
4. The compound, 9-(3-chloro-4-trifluoromethylphenyl)-8,10,dioxo-4,1,7,9-thiatriazabicyclo[5.3.0]decane-4,4-dioxide.
5. The compound according to claim 1, 9-(3,5-dichlorophenyl)-8,10-dioxo-4,1,7,9-thiatriazabicyclo[5.3.0] decane-4,4-dioxide.
6. A composition for selectively controlling weeds in crops of cereals, maize, rice and rape-seed, which composition comprises as active substance an effective amount of a compound of formula I, according to claim 1, together with a suitable carrier therefor.
7. A method for controlling dicotyledonous weeds, which comprises applying to a field where dicotyledonous weeds have to be controlled an effective amount of a compound according to claim 1.
8. A method for controlling weeds of the Galium family which comprises applying to a field where such weeds have to be controlled, an effective amount of compound according to claim 1.
9. A method for selectively controlling weeds in crops of cereals, maize, rice and rape-seed, which comprises applying to areas where such crops grow an effective amount of a compound according to claim 1.
10. A method for controlling weeds, which comprises applying to areas where said weeds grow, an effective amount of a compound according to claim 1.

* * * * *